US009445777B2

(12) United States Patent
Kitamura

(10) Patent No.: US 9,445,777 B2
(45) Date of Patent: Sep. 20, 2016

(54) PROJECTION IMAGE GENERATION APPARATUS, PROGRAM AND METHOD

(75) Inventor: Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 454 days.

(21) Appl. No.: 13/636,528

(22) PCT Filed: Mar. 30, 2011

(86) PCT No.: PCT/JP2011/001935
§ 371 (c)(1),
(2), (4) Date: Sep. 21, 2012

(87) PCT Pub. No.: WO2011/122035
PCT Pub. Date: Oct. 6, 2011

(65) Prior Publication Data
US 2013/0009958 A1 Jan. 10, 2013

(30) Foreign Application Priority Data

Mar. 31, 2010 (JP) ................... 2010-082190

(51) Int. Cl.
*G06T 17/00* (2006.01)
*A61B 6/00* (2006.01)
(Continued)

(52) U.S. Cl.
CPC .............. *A61B 6/503* (2013.01); *A61B 6/032* (2013.01); *G06T 7/0083* (2013.01); *G06T 15/08* (2013.01);
(Continued)

(58) Field of Classification Search
CPC ................... G06T 15/08; G06T 2207/10081; G06T 2210/41; G06T 11/008; G06T 11/005; G06T 11/003; G06T 7/0081; G06T 2207/30101; G06T 2207/10124; G06T 2219/008; G06T 2219/028; G06T 15/00; G06T 2207/30048; G06T 3/0037; A61B 8/483; A61B 8/463; A61B 6/466; A61B 8/00; A61B 8/08; A61B 8/0883; A61B 8/14; A61B 8/523; A61B 2576/023; A61B 5/055; A61B 5/4884; A61B 5/7207; A61B 6/022; A61B 6/03; A61B 6/502; A61B 6/5211; A61B 8/13; A61B 8/462; A61B 8/466; A61B 8/48

See application file for complete search history.

(56) References Cited

U.S. PATENT DOCUMENTS 7,369,691 B2 5/2008 Kondo et al.
7,447,535 B2 11/2008 Lavi
(Continued)

FOREIGN PATENT DOCUMENTS

CN 101065771 10/2007
JP 2004-519306 7/2004
(Continued)

OTHER PUBLICATIONS

Friman, Ola, Milo Hindennach, and Heinz-Otto Peitgen. "Template-based multiple hypotheses tracking of small vessels." ISBI. 2008.*
(Continued)

*Primary Examiner* — Sultana M Zalalee
(74) *Attorney, Agent, or Firm* — Young & Thompson

(57) ABSTRACT

A structure extraction element obtains three-dimensional structure extraction data by extracting a tubular structure from volume data obtained by imaging a predetermined subject. A relating element relates positions on paths of a two-dimensional template representing a schematic diagram of a three-dimensionally branching tubular structure obtained by imaging a predetermined subject and positions on paths of the three-dimensional structure extraction data to each other. A projection image generation element generates a two-dimensional projection image by projecting voxel values of the tubular structure that is present on the paths of the three-dimensional structure extraction data onto corresponding positions on the paths of the two-dimensional template.

16 Claims, 9 Drawing Sheets

(51) Int. Cl.
*A61B 6/03* (2006.01)
*G09B 23/30* (2006.01)
*G06T 7/00* (2006.01)
*G06T 15/08* (2011.01)

(52) U.S. Cl.
CPC ..... *G09B 23/30* (2013.01); *G06T 2207/10072* (2013.01); *G06T 2207/20016* (2013.01); *G06T 2207/20072* (2013.01); *G06T 2207/30048* (2013.01); *G06T 2207/30101* (2013.01); *G06T 2207/30172* (2013.01); *G06T 2215/06* (2013.01)

(56) References Cited

U.S. PATENT DOCUMENTS

| | | | |
|---|---|---|---|
| 7,646,903 | B2 | 1/2010 | Kaftan et al. |
| 7,787,683 | B2* | 8/2010 | Khamene ........... G06K 9/00208 382/130 |
| 2004/0002660 | A1 | 1/2004 | Mielekamp |
| 2004/0249270 | A1 | 12/2004 | Kondo et al. |
| 2006/0235288 | A1 | 10/2006 | Lavi |
| 2006/0235669 | A1* | 10/2006 | Charbel et al. ................. 703/11 |
| 2007/0001879 | A1 | 1/2007 | Kaftan et al. |
| 2007/0019846 | A1* | 1/2007 | Bullitt ................... G06T 7/0014 382/128 |
| 2007/0038061 | A1* | 2/2007 | Huennekens .......... A61B 6/504 600/407 |
| 2008/0192997 | A1* | 8/2008 | Grass ................... G06T 11/008 382/128 |
| 2009/0022387 | A1 | 1/2009 | Shirahata et al. |
| 2009/0148008 | A1 | 6/2009 | Wiemker et al. |

FOREIGN PATENT DOCUMENTS

| | | |
|---|---|---|
| JP | 2004-283373 | 10/2004 |
| JP | 2007-501045 | 1/2007 |
| JP | 2007-044488 | 2/2007 |
| JP | 2008-520319 | 6/2008 |
| WO | WO 2007/122896 | 11/2007 |

OTHER PUBLICATIONS

Groher, Martin. 2D-3D Registration of Vascular Images. Diss. Dissertation, Technische Universität München, München, 2008.*
Chillet, Dini, et al. "Vascular atlas formation using a vessel-to-image affine registration method." Medical Image Computing and Computer-Assisted Intervention-MICCAI 2003. Springer Berlin Heidelberg, 2003. 335-342.*
International Search Report, PCT/2011/001935, May 17, 2011.
A. Kanitsar et al., "CPR-Curved Planar Reformation", VIS 2002. IEEE, pp. 37-44, 2002.
A. Szymczak et al., "Coronary vessel trees from 3D imagery: A topological approach", Medical Image Analysis, vol. 10, pp. 548-559 2006.
A. Kanitsar et al., "Advanced Curved Planar Reformation: Flattening of Vascular Structures", VIS 2003. IEEE, pp. 43-50, 2003.
CN Office Action dated May 5, 2014, with English Translation; Application No. 201180016611.X.
JP Office Action dated Sep. 3, 2013, with partial English translation; Application No. 2010-082190.
Chinese Office Action dated Dec. 15, 2015; Application No. 201180016611.X.

* cited by examiner

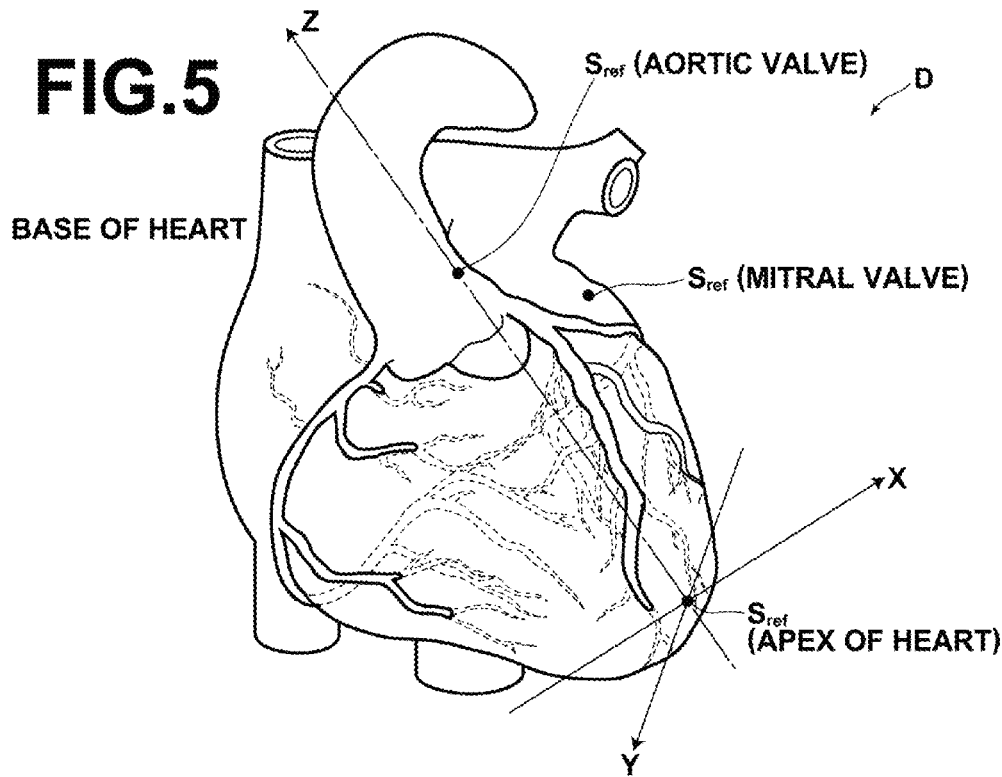
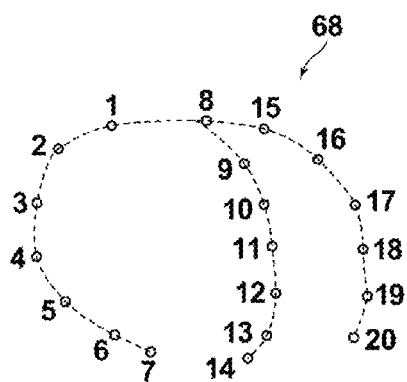

FIG.16
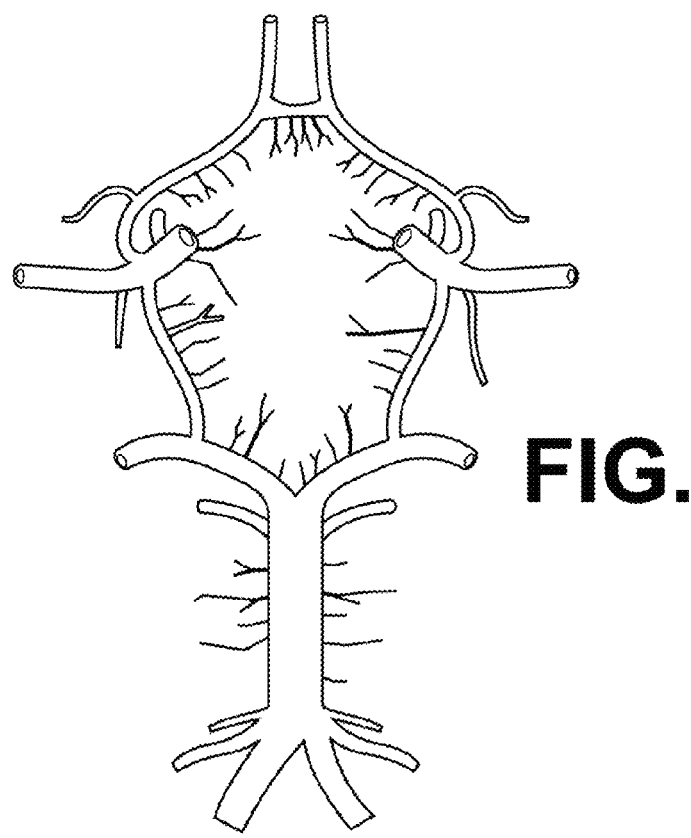
FIG.17

PROJECTION IMAGE GENERATION APPARATUS, PROGRAM AND METHOD

BACKGROUND OF THE INVENTION

1. Field of the Invention

The present invention relates to a projection image generation apparatus, program and method for generating a projection image by projecting a three-dimensional tubular anatomical structure in three-dimensional data onto a two-dimensional plane.

2. Description of the Related Art

In recent years, high-quality three-dimensional images (volume data) became used in image-based diagnosis as medical equipment (for example, a multi-detector CT, or the like) advanced. Volume data are composed of many two-dimensional images, and the information amount of the volume data is large. Therefore, in some cases, a doctor needs a time to find a desired observation region to diagnose a patient. Therefore, an improvement of a characteristic of recognizing a whole organ and a lesion was attempted by extracting and displaying an organ of interest by MIP, VR, CPR, or the like, thereby improving the efficiency of diagnosis.

Especially, Curved Planar Reconstruction (CPR) is known as an effective display method for observing a tubular structure in volume data (for example, please refer to A. Kanitsar et al., "CPR-Curved Planar Reformation", VIS 2002. IEEE, pp. 37-44, 2002 (Non-Patent Document 1)). The CPR generates an image by sequentially reconstructing, along a path that a user wants to display, projection surfaces in directions orthogonal to the path. However, when tubular structures of branching plural paths are displayed at the same time, there is an unobservable region in some cases, because the paths overlap each other. Therefore, an Untangle CPR method has been proposed (for example, please refer to A. Kanitsar et al., "Advanced Curved Planar Reformation: Flattening of Vascular Structures", VIS 2003. IEEE, pp. 43-50, 2003 (Non-Patent Document 2)). The Untangled CPR method displays an image by branching paths based on a certain rule in such a manner that the paths do not overlap each other.

When blood vessels are extracted from volume data and projected onto a CPR image, cross-sections of the blood vessels are displayed on the CPR image. Therefore, the CPR image is appropriate to observe a stenosis region of a blood vessel, which is caused by a plaque or the like. However, in the method of Non-Patent Document 1, an unobservable region is generated in some cases, because paths overlap each other. Meanwhile, in the method of Non-Patent Document 2, paths do not overlap each other. However, when a three-dimensional branching portion of blood vessels is expanded two-dimensionally, the blood vessels are displayed in such a manner to branch based on a predetermined rule. Therefore, a corresponding relationship with an actual anatomical position becomes unclear, and even if a stenosis region in a blood vessel is recognized in a CPR image, there is a problem that it is difficult to recognize at which position the stenosis has occurred in actual coronary arteries.

SUMMARY OF THE INVENTION

In view of the foregoing circumstances, it is an object of the present invention to provide a projection image generation apparatus, program and method for generating a projection image in which an anatomical position in a tubular structure displayed on a two-dimensional plane is recognizable, while the three-dimensionally-branching tubular structures are projected onto the two-dimensional plane in such a manner that they do not overlap each other.

A projection image generation apparatus of the present invention is characterized by comprising:

a two-dimensional template storage means that stores a two-dimensional template that two-dimensionally represents a schematic diagram of each path of a tubular structure composed of a plurality of three-dimensionally branching paths, and in which a corresponding relationship of anatomical positions between positions on the paths of the tubular structure and positions on paths of the two-dimensional template has been set in advance;

a structure extraction means that obtains three-dimensional structure extraction data by extracting the tubular structure from volume data obtained by imaging a predetermined subject;

a relating means that relates, based on the corresponding relationship, the positions on the paths of the two-dimensional template and the positions on the paths of the three-dimensional structure extraction data to each other; and a projection image generation means that generates a two-dimensional projection image by projecting voxel values of the tubular structure that is present on the paths of the three-dimensional structure extraction data onto corresponding positions on the paths of the two-dimensional template.

A projection image generation program of the present invention is characterized by causing a computer to function as:

a two-dimensional template readout means that reads out a two-dimensional template from a two-dimensional template storage means storing the two-dimensional template that two-dimensionally represents a schematic diagram of each path of a tubular structure composed of a plurality of three-dimensionally branching paths, and in which a corresponding relationship of anatomical positions between positions on the paths of the tubular structure and positions on paths of the two-dimensional template has been set in advance;

a structure extraction means that obtains three-dimensional structure extraction data by extracting the tubular structure from volume data obtained by imaging a predetermined subject;

a relating means that relates, based on the corresponding relationship, the positions on the paths of the two-dimensional template and the positions on the paths of the three-dimensional structure extraction data to each other; and a projection image generation means that generates a two-dimensional projection image by projecting voxel values of the tubular structure that is present on the paths of the three-dimensional structure extraction data onto corresponding positions on the paths of the two-dimensional template.

A projection image generation method of the present invention is characterized by executing, by a computer:

two-dimensional template readout processing that reads out a two-dimensional template from a two-dimensional template storage means storing the two-dimensional template that two-dimensionally represents a schematic diagram of each path of a tubular structure composed of a plurality of three-dimensionally branching paths, and in which a corresponding relationship of anatomical positions between positions on the paths of the tubular structure and positions on paths of the two-dimensional template has been set in advance;

structure extraction processing that obtains three-dimensional structure extraction data by extracting the tubular structure from volume data obtained by imaging a predetermined subject;

relating processing that relates, based on the corresponding relationship, the positions on the paths of the two-dimensional template and the positions on the paths of the three-dimensional structure extraction data to each other; and projection image generation processing that generates a two-dimensional projection image by projecting voxel values of the tubular structure that is present on the paths of the three-dimensional structure extraction data onto corresponding positions on the paths of the two-dimensional template.

The term "a schematic diagram of a structure" refers to a diagram drawn in such a manner that a substantial part of the structure and the characteristic of the structure are emphasized. Further, the phrase "a schematic diagram of each path of a tubular structure" refers to a diagram illustrating an anatomical characteristic, such as an anatomical position of each path of the tubular structure and the diameter of each path.

Further, the expression "a corresponding relationship of anatomical positions between positions on the paths of the tubular structure and positions on paths of the two-dimensional template" refers to a relationship in which positions in a three-dimensionally-branching tubular structure in three-dimensional space and positions in a tubular structure of a two-dimensional template in two-dimensional space, the anatomical characteristics of which agree with each other, are related to each other. For example, when the tubular structure is coronary arteries, it is desirable that corresponding relationships of the positions of aright coronary artery (RCA), a left main coronary artery (LCA), a left anterior descending branch (LAD), a left circumflex branch (LCX) and the like are recognizable so that anatomical positions in the coronary arteries are recognized.

It is desirable that the projection image generation means includes a first projection means that projects the voxel values of the tubular structure of the three-dimensional structure extraction data onto a ribbon-shaped projection surface defined along the paths of the three-dimensional structure extraction data in three-dimensional space, and a second projection means that performs projection after transforming an image that has been projected onto the ribbon-shaped projection surface by the first projection means to a shape on a corresponding path of the two-dimensional template.

It is desirable that the projection image generation means performs projection onto the corresponding positions on the paths of the two-dimensional template in such a manner that information about the diameter of the tubular structure that is present on the paths of the three-dimensional structure extraction data is maintained.

The expression "information about the diameter of the tubular structure is maintained" means that projection is performed in such a manner that a ratio of the diameter of the tubular structure at a predetermined position of three-dimensional structure extraction data to the width of a projection image of the tubular structure on a two-dimensional template corresponding to the position is always the same.

The projection image generation means may change the length of the corresponding path of the two-dimensional template in such a manner that information about the length of the tubular structure of the three-dimensional structure extraction data is maintained.

The expression "the length of the tubular structure is maintained" means that projection is performed by changing the length of each path of the two-dimensional template in such a manner that a ratio of the length of a predetermined path of the tubular structure of three-dimensional structure extraction data to the length of a path on a two-dimensional template corresponding to the path does not change.

The two-dimensional template may be a schema diagram representing an anatomical characteristic of the tubular structure.

Further, the tubular structure may be blood vessels.

According to a projection image generation apparatus, a projection image generation program and a projection image generation method of the present invention, it is possible to easily recognize an abnormal position, such as a stenosis region, that is present on a path of a tubular structure by generating a two-dimensional projection image by projecting the tubular structure extracted from volume data onto a path on a two-dimensional template representing a schematic diagram of the tubular structure, and in which an anatomical position has been set in advance.

Further, it is possible to display an image in such a manner that branching paths do not overlap each other by performing projection after transforming an image that has been projected onto a ribbon-shaped projection surface defined along a path of a tubular structure in three-dimensional space to a shape on a corresponding path of a two-dimensional template.

Further, it is possible to observe a change in a diameter by projecting an image onto a two-dimensional template in such a manner that information about the diameter of a tubular structure that is present on a path is maintained. Further, it is possible to observe a change in the diameter of a blood vessel or the like, and to check whether a stenosis region is present.

Further, when the length of a path of a two-dimensional template is changed in such a manner to maintain information about the length of a tubular structure that is present on the path as well as information about the diameter of the tubular structure, it is possible to observe the tubular structure in a state similar to an actual state of each subject.

When the two-dimensional template is a schema diagram, an observer, such as a doctor, can easily recognize a diseased region by using a familiar image.

BRIEF DESCRIPTION OF THE DRAWINGS

FIG. 5 is a diagram illustrating an example of definition of a reference coordinate system.

FIG. 6 is a diagram illustrating an example of connection relationships between reference points in a two-dimensional template.

FIG. 16 is a diagram illustrating an example of a projection image output on a display screen.

FIG. 17 is a diagram illustrating an example of a tubular structure including a closed path.

DESCRIPTION OF THE PREFERRED EMBODIMENTS

Hereinafter, embodiments of a projection image generation apparatus and a projection image generation program and method according to the present invention will be described in detail with reference to drawings.

Figure 1:
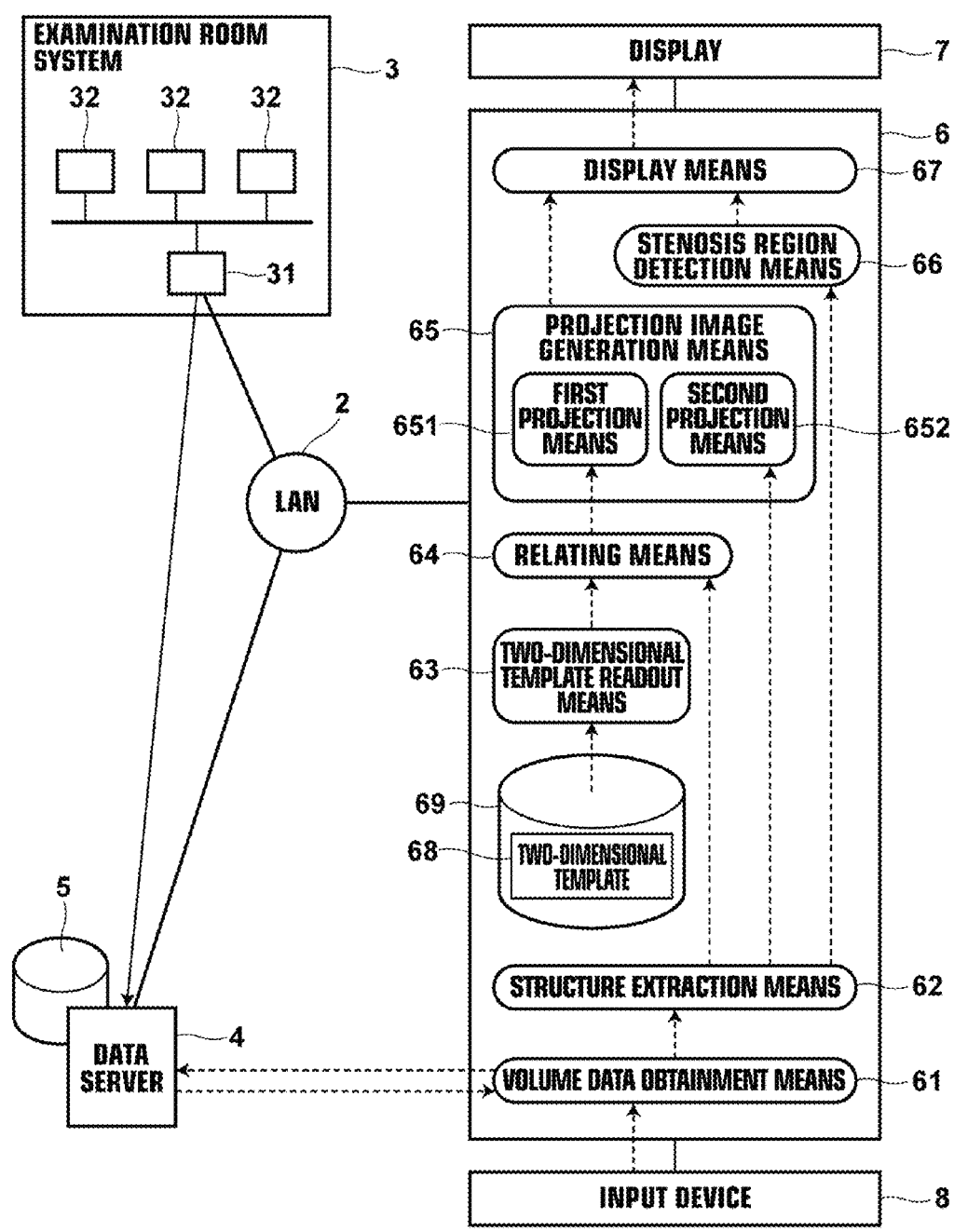
FIG. 1 is a schematic diagram illustrating the configuration of a projection image generation apparatus according to an embodiment of the present invention.

FIG. 1 is a schematic diagram illustrating the configuration of a hospital system including a projection image generation apparatus according to an embodiment of the present invention. The hospital system 1 includes an examination room system 3, a data server 4 and a workstation (WS) 6 for diagnosis, which are connected to each other through a local area network (LAN) 2.

The examination room system 3 includes various modalities 32 for imaging a subject to be examined and an examination room workstation (WS) 31. The examination room workstation (WS) 31 is used to check and adjust an image output from each modality. As the modalities 32, for example, an X-ray radiography apparatus, a CT (Computed Tomography) apparatus, an MRI (Magnetic Resonance Imaging) apparatus, a PET (Positron Emission Tomography), and the like are provided. All of these modalities are based on DICOM (Digital Imaging and Communication in Medicine) standard. The modalities 32 output obtained volume data as a DICOM file after attaching supplementary information to the volume data.

A file is output from a modality 32, and transferred to the data server 4 by the examination room WS 31. The data server 4 is a relatively high processing power computer including a high performance processor and a large capacity memory, and a software program for providing a database management server (DBMS: Detabase Management Server) function has been implemented in the computer. The program is stored in a storage, and loaded into the memory at boot-up. Further, the program is executed by a processor. The data server 4 stores the file transferred from the examination room WS 31 in a large capacity storage 5. Further, the data server 4 selects, based on a search request from the WS 6 for diagnosis, a file appropriate for a search condition from plural files stored in the large capacity storage 5, and sends the selected file to the WS 6 for diagnosis.

The WS 6 for diagnosis is a general-purpose workstation including a standard processor, a memory and a storage, and in which a projection image generation program for supporting diagnosis has been implemented. The projection image generation program is installed in the WS 6 for diagnosis from a recording medium, such as a DVD, or downloaded from a server computer in a network and installed in the WS 6 for diagnosis. Further, a display 7 and an input device 8, such as a mouse and a keyboard, are connected to the WS 6 for diagnosis.

The projection image generation program implemented in the WS 6 for diagnosis is composed of program module groups for realizing various functions including a program module group for realizing a projection image generation function. These programs are stored in a storage, and loaded into a memory at boot-up, and executed by a processor. Accordingly, the WS 6 for diagnosis operates as a volume data obtainment means 61, a structure extraction means 62, a two-dimensional template readout means 63, a relating means 64, a projection image generation means 65, a stenosis region detection means 66 and a display means 67, which are illustrated in FIG. 1.

Further, a two-dimensional template 68 is stored in the storage of the WS 6 for diagnosis, and the storage functions as a two-dimensional template storage means 69.

In the present embodiment, examination of a heart will be used as an example, and a case in which a tubular structure is a blood vessel, especially, coronary arteries will be described.

In examination of a heart, the chest of a subject is imaged by a CT apparatus or the like to obtain volume data. Further, supplementary information is attached to the volume data, and the volume data are transferred as a DICOM file to the data server 4. The volume data are stored in the large capacity storage 5. The volume data are composed of a set of many sets of voxel data representing voxel values and a density distribution of the voxel value in three-dimensional space, and an absorption amount of X-rays or the like is represented, as a voxel value, in each voxel data.

Next, processing by each means constituting the WS 6 for diagnosis will be described. A function to generate a projection image of a heart is selected in an initial screen, and an identification number of a patient, an examination number or the like is input in a predetermined input screen. Then, the volume data obtainment means 61 sends the input information to the data server 4, and requests the data server 4 to search the large capacity storage 5 for a stored file, and to transfer the file.

When the data server 4 receives the request, the data server 4 searches the large capacity storage 5 for the file, and transfers the requested file to the volume data obtainment means 61. The volume data obtainment means 61 stores volume data included in the file transferred from the data server 4 in the memory.

The structure extraction means 62 extracts a coronary artery region, i.e., a region corresponding to walls of blood vessels of coronary arteries and lumens of the blood vessels of the coronary arteries from the volume data stored in the memory by the aforementioned processing, and obtains three-dimensional structure extraction data. In the process of extracting the coronary artery region, paths of the coronary arteries are identified.

Next, processing for extracting the coronary arteries will be further described. As a method for extracting a coronary artery region from volume data, various methods, such as a method disclosed in A. Szymczak et al., "Coronary vessel trees from 3D imagery: A topological approach", Medical Image Analysis, Vol. 10, pp. 548-559, 2006, have been proposed. In extraction of a region, any known method may be adopted. However, in the present embodiment, methods proposed in Japanese Patent Application No. 2009-048679 and Japanese Patent Application No. 2009-069895 by the applicant will be used. Next, processing described in these documents will be outlined.

Figure 2:
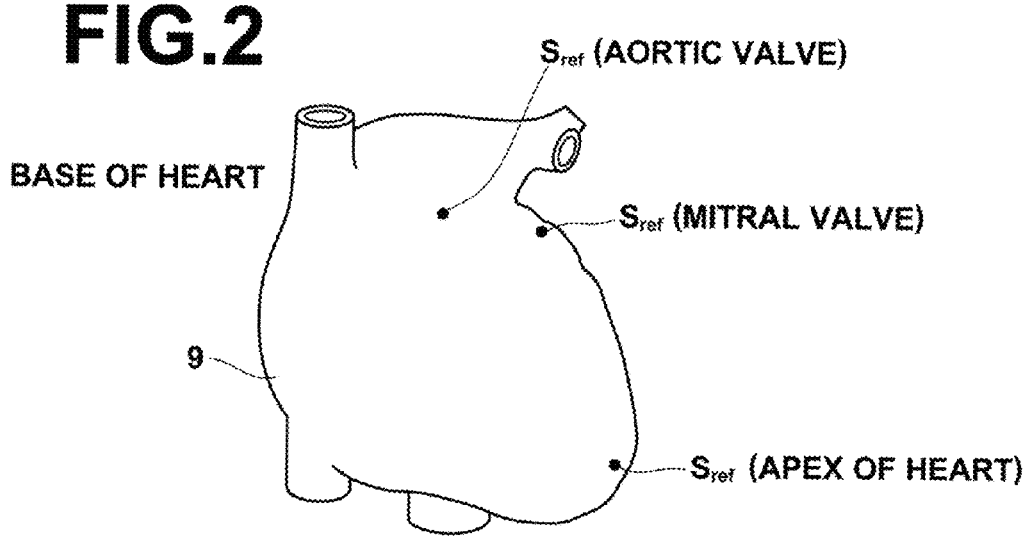
FIG. 2 is a diagram illustrating an example of a heart region extracted by a structure extraction means.

The structure extraction means 62 extracts, based on a predetermined algorithm, a region (hereinafter, a heart region) corresponding to the heart from volume data. FIG. 2 illustrates a heart region 9 extracted by the structure extraction means 62. As illustrated in FIG. 2, in the process of extracting the heart region 9, positions $S_{ref}$ such as the position of an aortic valve, the position of a mitral valve, and the position of the apex of heart, which characterize the shape of the heart, are also identified. The coordinates of the identified positions are stored in the memory, and used when a reference coordinate system is defined in processing that will be described later.

Figure 3:
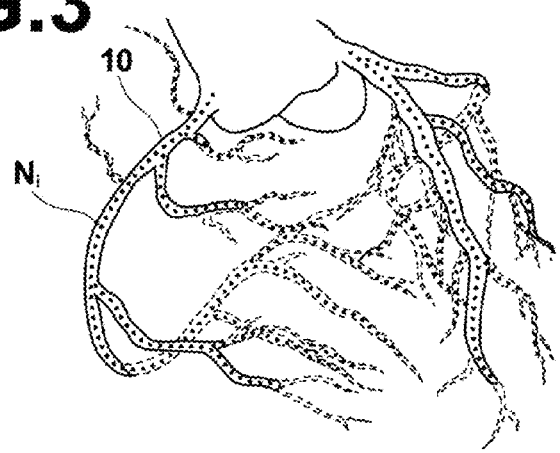
FIG. 3 is a diagram illustrating an example of candidate points detected by the structure extraction means.

Next, the structure extraction means 62 sets, as a search range, a rectangular-parallelopiped region including the heart region 9 in the volume data, and searches the search range for a tubular structure included in the search range based on a predetermined algorithm. Further, the structure extraction means 62 detects, based on the tubular structure that has been detected by search, points estimated to be points on core lines of the coronary arteries. In the following descriptions, a point estimated to be a point on a path of the coronary artery will be referred to as a candidate point, or a node. FIG. 3 illustrates an extracted tubular structure 10 of three-dimensional structure extraction data, and detected candidate points Ni.

A tubular structure is searched for by calculating eigenvalues of 3×3 Hessian (Hessian) matrix for each local region in the search range. In a region including a tubular structure, one of three eigenvalues of a Hessian matrix is a value close to 0, and the other two eigenvalues are relatively large values. Further, an eigenvector corresponding to the eigenvalue close to 0 represents the direction of the principal axis of the tubular structure. The structure extraction means 62 judges, based on eigenvalues of a Hessian matrix, a likelihood of a tubular structure for each local region. The structure extraction means 62 detects, as a candidate point, the center point of a local region in which a tubular structure has been identified.

In search for a tubular structure, it is desirable that plural sets of data for respective resolutions (Gaussian pyramid) are generated at different resolutions by converting the resolution of data in a search range, and search (scan) is repeated at different resolutions. In the aforementioned search method, when the diameter (width) of a local region is less than the diameter of a blood vessel, it is impossible to identify the tubular structure. However, when search is performed at different resolutions, it is possible to identify a tubular structure in any size. Accordingly, it is possible detect all candidate points including a major large-diameter blood vessel and a terminal small-diameter blood vessel.

Figure 4:
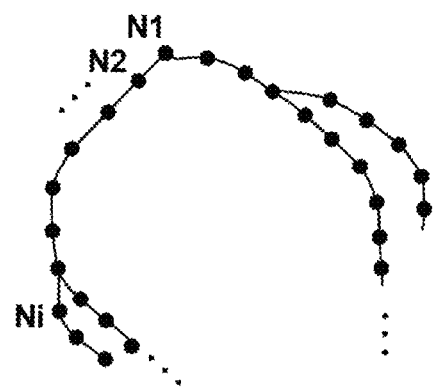
FIG. 4 is a diagram illustrating a tree structure constructed by connecting extracted candidate points.

Next, the structure extraction means 62 connects, based on a predetermined algorithm such as spline interpolation processing, the candidate points detected by search. Accordingly, a tree structure composed of the candidate points and branches (edges) connecting the candidate points together is constructed, as illustrated in FIG. 4. Coordinate information about the detected plural candidate points and vector information representing the direction of a branch are stored in the memory together with the identifiers of the candidate points and the branches.

Then, the structure extraction means 62 identifies the shape of the coronary arteries in detail based on voxel values (CT values) in the vicinity of each detected candidate point. Specifically, the structure extraction means 62 identifies the contour of a coronary artery (the outer wall of a blood vessel) in a cross section perpendicular to the path of the coronary artery. The shape is identified by using a known segmentation method, typified by Graph-Cuts.

Finally, the structure extraction means 62 defines a reference coordinate system by using, as reference positions, positions $S_{ref}$ of the aortic valve, the mitral valve, and the apex of heart that have been stored in the process of identifying the heart region 9. For example, as illustrated in FIG. 5, the apex of heart is used as an origin of the reference coordinate system, and a direction from the apex of heart toward the aortic valve is set as Z-axis. Further, X-axis and Y-axis are defined based on a relationship with the mitral valve. Further, the scale of the coordinate system is normalized by defining a length from the apex of heart to the aortic valve as 1. Further, the coordinate values that have been stored in the memory in the aforementioned processing are converted into coordinate values in the reference coordinate system. Specifically, data representing the positions of the candidate points and the branches, the contour of the coronary artery and the like are normalized. The normalized information is stored in the memory in such a manner to be related to information before normalization. In the following descriptions, the normalized data about the candidate points and the contour are described as three-dimensional structure extraction data D.

Next, processing of the relating means 64 will be described. The relating means 64 relates positions on paths of the tubular structure 10 of the three-dimensional structure extraction data D extracted by the structure extraction means 62 to positions on paths of the two-dimensional template 68. First, before processing is performed by the relating means 64, the second-dimensional template readout means 63 reads out the two-dimensional template 68 from the storage of the WS 6 for diagnosis, and stores the two-dimensional template 68 in the memory.

Figure 7:
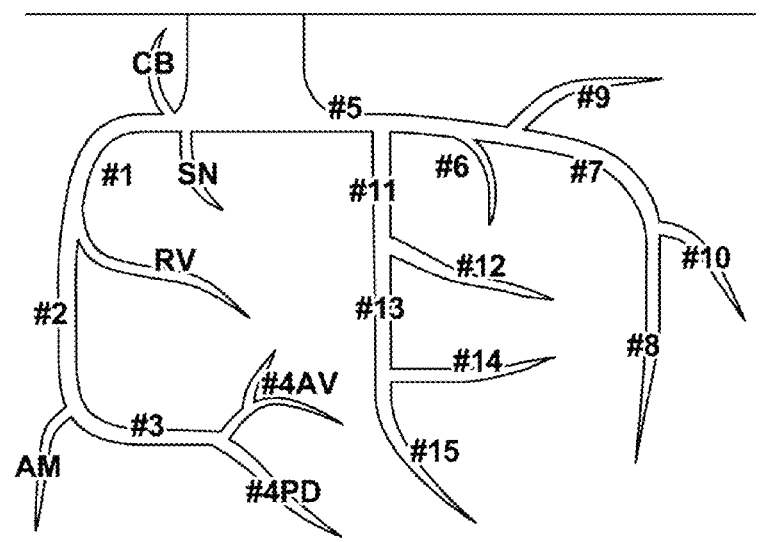
FIG. 7 is an example of a schema diagram of coronary arteries.

The two-dimensional template 68 is a schematic diagram two-dimensionally representing each path of coronary arteries. In the two-dimensional template 68, a corresponding relationship of anatomical positions between a position on a path of the coronary arteries in three-dimensional space and a position on a path of the two-dimensional template 68 is set in advance. Specifically, the two-dimensional template 68 is composed of plural reference points and a connection relationship between the reference points. The plural reference points are defined at a branching position and a relay point of each path, which represent an anatomical characteristic of a three-dimensionally branched blood vessel structure. Especially, the positions of a right coronary artery (RCA), a left main coronary artery (LCA), a left anterior descending branch (LAD), a left circumflex branch (LCX) and the like are important positions representing the anatomical characteristic. Therefore, it is desirable that these positions are set as reference points of the two-dimensional template 68. FIG. 6 illustrates an example of reference points (white circles in FIG. 6) on three paths of coronary arteries in the two-dimensional template 68 and a connection relationship between the reference points (a broken line in FIG. 6). The connection relationship is defined by a smooth curve passing through the reference points by using an algorithm, such as spline interpolation processing. The two-dimensional template 68 should make it possible to recognize anatomical characteristic positions in coronary arteries, and to which branched path of coronary arteries a blood vessel corresponds. For example, the shape of a schema diagram of the coronary arteries illustrated in FIG. 7 may coincide with the shape of the two-dimensional template 68.

The relating means 64 of the present embodiment prepares three-dimensional model M of coronary arteries representing paths of coronary arteries, and a three-dimensional-two-dimensional corresponding position information. The three-dimensional-two-dimensional corresponding position information defines, in advance, corresponding positions between positions on paths of the three-dimensional model M of coronary arteries and positions on paths of the two-dimensional template 68. First, the relating means 64 relates positions of coronary arteries of three-dimensional structure extraction data D and positions of coronary arteries in the three-dimensional model M of coronary arteries to each other. After then, the relating means 64 relates the positions in the coronary arteries of the three-dimensional structure extraction data D and positions in coronary arteries in the two-dimensional template 68 to each other by using the three-dimensional-two-dimensional corresponding position information. This case will be described.

The three-dimensional model M of coronary arteries is a three-dimensional model defining, in three-dimensional space, the position of a region representing a characteristic of the shape of the heart, each path of coronary arteries and the diameter of blood vessels in a standard heart. Specifically, in the three-dimensional model M of coronary arteries, positions $S_{ref}$, such as the position of an aortic valve, the position of a mitral valve, and the position of the apex of heart, which characterize the shape of the heart, reference points on the paths of coronary arteries and branches connecting the reference points to each other are defined in advance. Further, reference points in the three-dimensional model M of coronary arteries and reference points in the two-dimensional template 68 are related to each other in advance. Further, a reference coordinate system is defined also in the three-dimensional model M of coronary arteries by using, as reference positions, the positions $S_{ref}$ of the aortic valve, the mitral valve, and the apex of heart so that the three-dimensional model M of coronary arteries is related to the coronary artery region of the three-dimensional structure extraction data D. Further, in a manner similar to the three-dimensional structure extraction data D illustrated in FIG. 5, the apex of heart is used as an origin of the reference coordinate system, and a direction from the apex of heart toward the aortic valve is set as Z-axis. Further, X-axis and Y-axis are defined based on the relationship with the mitral valve. Further, a length from the apex of heart to the aortic valve is defined as 1.

Figure 8:
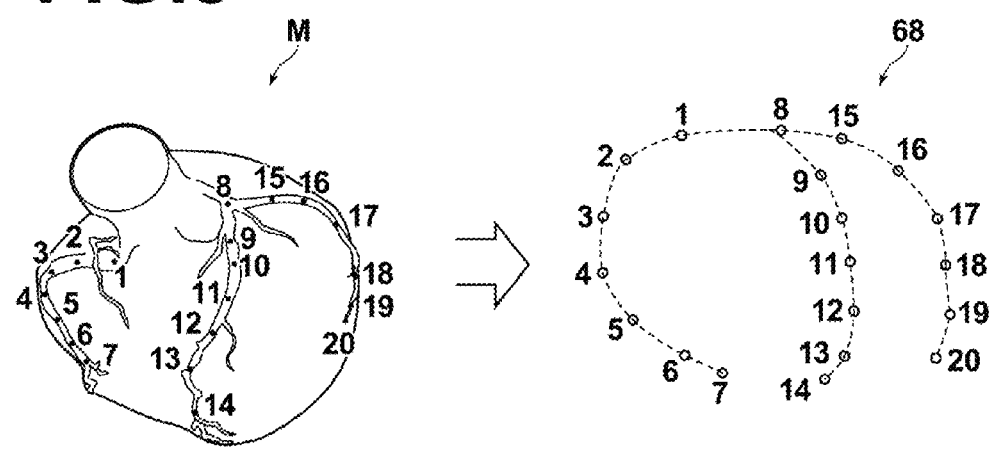
FIG. 8 is a diagram illustrating correspondence between reference points in a three-dimensional model of coronary arteries and reference points in a two-dimensional template.

FIG. 8 illustrates an example of correspondence between reference points in three-dimensional model M of coronary arteries and reference points in the two-dimensional template 68. Points to which numbers are assigned represent reference points, and the same number is assigned to a reference point in the three-dimensional model M of coronary arteries and a reference point in the two-dimensional template 68 when the anatomical positions of the reference points are the same. This corresponding relationship is stored as three-dimensional-two-dimensional corresponding relationship information.

Figure 9:
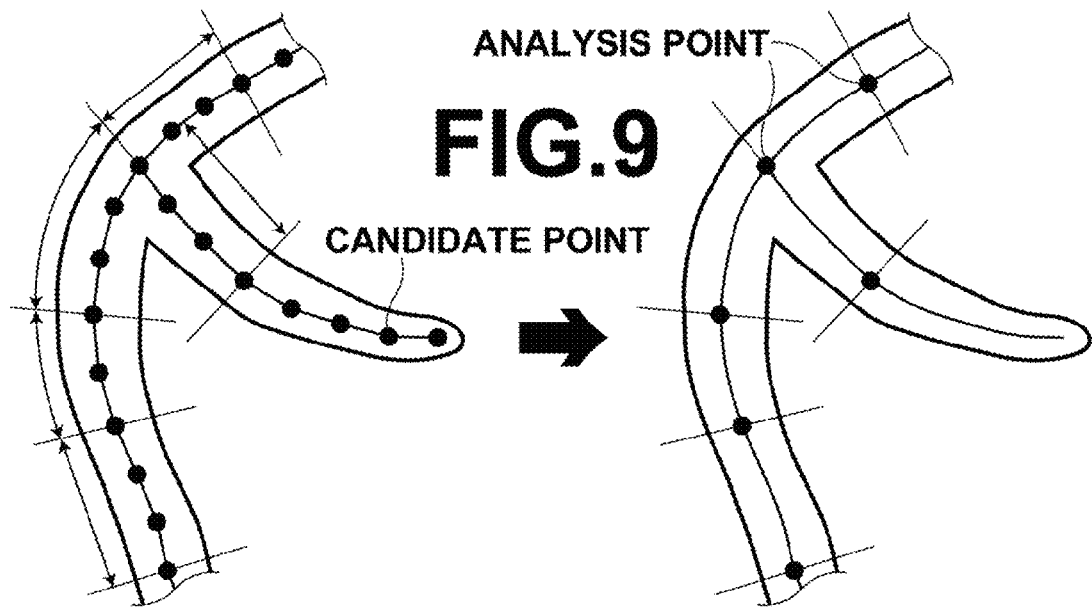
FIG. 9 is a diagram illustrating an example of setting analysis points.

First, the relating means 64 relates the coronary arteries of the three-dimensional structure extraction data D and the three-dimensional model M of coronary arteries to each other. Specifically, points the coordinates of the positions of which differ from each other in reference coordinate systems, but the positions of which are anatomically the same are related to each other. Points may be related to each other with respect to all candidate points constituting a tree structure. However, in the present embodiment, a part of the candidate points of the three-dimensional structure extraction data D are set as analysis points, as illustrated in FIG. 9, and only the set analysis points are related. The analysis points are set in the following manner.

The relating means 64 segments a tree structure that is specified by candidate points and branches. In the present embodiment, a candidate point connected to three or more branches, in other words, a candidate point located at a branching point of blood vessels is set as a boundary between segments. Further, candidate points that are present on an extension line of a branch extending from the branching point and the branch are divided into each segment having a predetermined number of candidate points or a predetermined length. Further, a candidate point located at a boundary between segments is selected as an analysis point. The relating means 64 stores information (the coordinate of a position or an identifier of a candidate point) that is necessary for the relating means 64 to identify an analysis point in the memory. Accordingly, the analysis points are set.

After the analysis points are set, the relating means 64 relates, by using a graph matching method, an analysis point in the three-dimensional structure extraction data D and a reference point in the three-dimensional model M of coronary arteries that are estimated to be anatomically the same points to each other. In the present embodiment, the relating means 64 calculates the degree of similarity of an analysis point set on a path of coronary arteries based on a predetermined evaluation function. Further, the relating means 64 relates an analysis point having a highest degree of similarity in the three-dimensional structure extraction data D and a reference point in the three-dimensional model M of coronary arteries to each other. The evaluation function is defined, while the coordinate of a position in a reference coordinate system, the number of candidate points connected to the analysis point and the coordinate values of the candidate points, the diameters of blood vessels in the vicinity of the analysis point, and the like are considered. In this case, it is desirable that the number and the kind of elements to be considered are defined, while a balance of the accuracy of evaluation and a processing time are considered.

Meanwhile, various methods have been proposed to relate an anatomical structure by graph matching, for example, as disclosed in Japanese Unexamined Patent Publication No. 2007-044488. Other known methods may also be used to relate an analysis point and a reference point to each other.

Finally, the relating means 64 relates the analysis point in coronary arteries of the three-dimensional structure extraction data D to the reference point in the two-dimensional template 68 by using three-dimensional-two-dimensional corresponding position information.

Next, processing of the projection image generation means 65 will be described. The projection image generation means 65 projects voxel values of a tubular structure that is present on a path of three-dimensional structure extraction data D to corresponding positions on a path of the two-dimensional template 68, and generates a two-dimensional projection image.

The projection image generation means 65 defines a ribbon-shaped projection surface along the path of coronary arteries of the three-dimensional structure extraction data D in three-dimensional space. The projection image generation means 65 performs processing by a first projection means 651 for projecting voxel values of the coronary arteries of the three-dimensional structure extraction data D onto the projection surface. After then, the projection images generation means 65 performs processing by a second projection means 652. In the processing by the second projection means 652, the shape of an image projected onto the ribbon-shaped projection surface by projection of the voxel values is transformed to a shape on a corresponding path of the two-dimensional template 68, and projection is performed.

Figure 10:
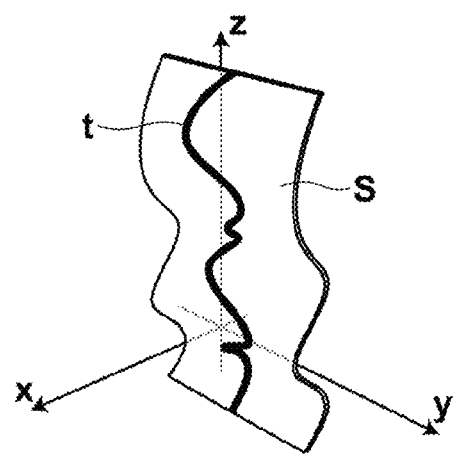
FIG. 10 is a diagram for explaining a method for projecting a tubular structure.

The first projection means 651 defines ribbon-shaped projection surface S, as illustrated in FIG. 10, in such a manner that the ribbon-shaped projection surface S extends along principal axis t, which substantially passes the center of the coronary arteries extracted by the structure extraction means 62. An XY plane perpendicular to the principal axis t is set, and projection surface S is defined, for example, as a set of lines extending in the direction of Y-axis. A GUI for specifying a direction of this projection surface S with respect to the principal axis may be provided so that an observer can input the projection surface S in a direction in which the observer wants to observe by rotating X-axis and Y-axis in an arbitrary direction with respect to the principal axis t, as a center. It is desirable that the observer can indicate the direction of the projection surface S at each reference point of the two-dimensional template 68 for each path of a branching point.

Figure 11A:
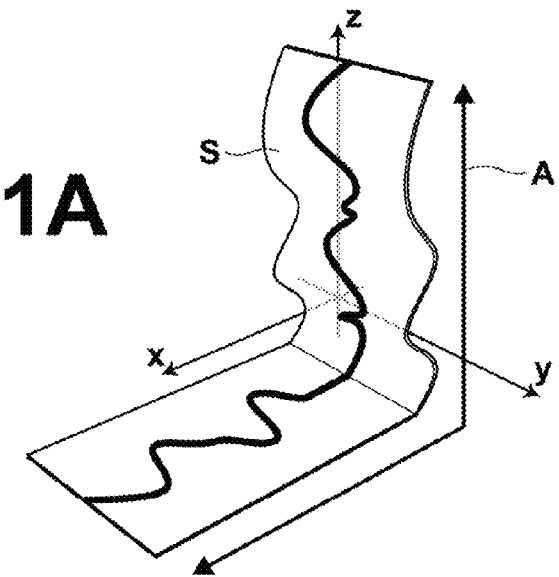
FIG. 11A is a diagram for explaining a projection image generated by a Projected CPR method.
Figure 11B:
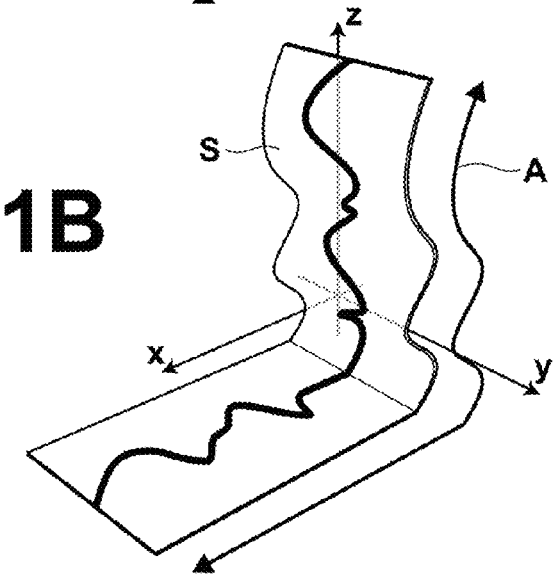
FIG. 11B is a diagram for explaining a projection image generated by a Stretched CPR method.
Figure 11C:
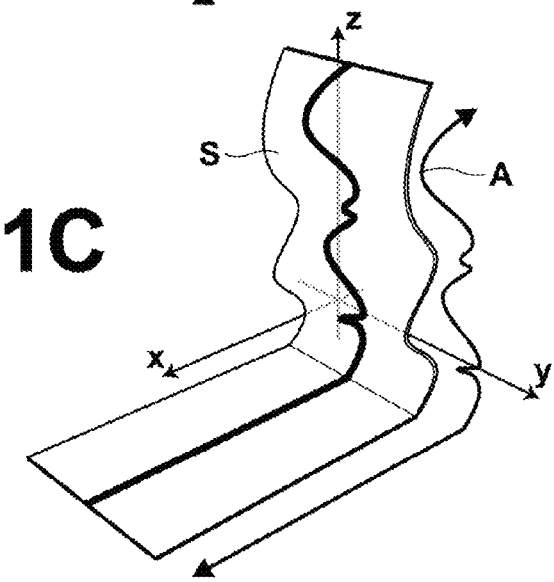
FIG. 11C is a diagram for explaining a projection image generated by a Straightened CPR method.

Next, a CPR image is generated by projecting voxel values of coronary arteries onto the defined projection surface S. As a method for generating a CPR image, there are three methods for generating a CPR image, as illustrated in FIGS. 11A, 11B, and 11C. An image on a horizontal plane in each of FIGS. 11A, 11B and 11C represents an image obtained by projecting a tubular structure onto a surface defined by upward thick arrow A and Y-axis. FIG. 11A illustrates an image generated by a Projected CPR method. FIG. 11B illustrates an image generated by a Stretched CPR method. FIG. 11C illustrates an image generated by a Straightened CPR method (please refer to Non-Patent Document 1 for the detail of the CPR image generation method). The first projection means 651 may use any of the CPR image generation methods.

Figure 12:
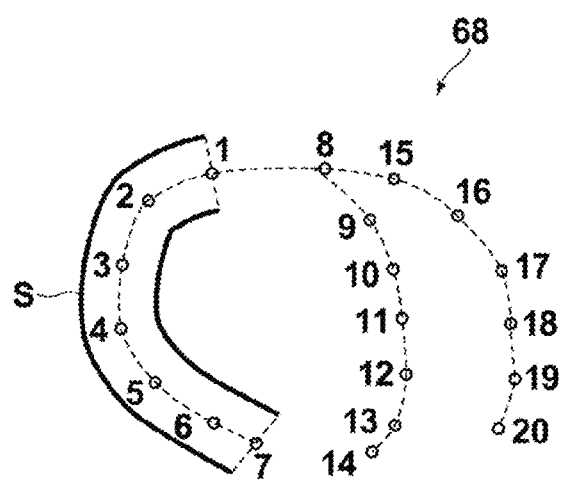
FIG. 12 is a diagram illustrating a manner of transforming an image that has been projected onto a ribbon-shaped projection surface to conform to reference points of a two-dimensional template (No. 1).

Next, the second projection means 652 transforms the CPR image generated by the first projection means 651 to a shape on a corresponding path of the two-dimensional template 68, and performs projection. Specifically, the second projection means 652 transforms, based on analysis points on the coronary arteries of the three-dimensional structure extraction data D, and which have been related to reference points of the two-dimensional template 68, a CPR image of each coronary artery projected onto the ribbon-shaped projection surface S. The CPR image is transformed in such a manner that the CPR image extends along the shape of a corresponding path of the two-dimensional template 68. FIG. 12 illustrates a manner of transforming an image that has been projected onto the ribbon-shaped projection surface S in such a manner to conform to the shape of the two-dimensional template 68 so that the analysis points and the reference points coincide with each other. Meanwhile, in the example illustrated in FIG. 12, there is a region in which a ribbon is not set on the two-dimensional template 68, and onto which projection is not performed.

Figure 13:
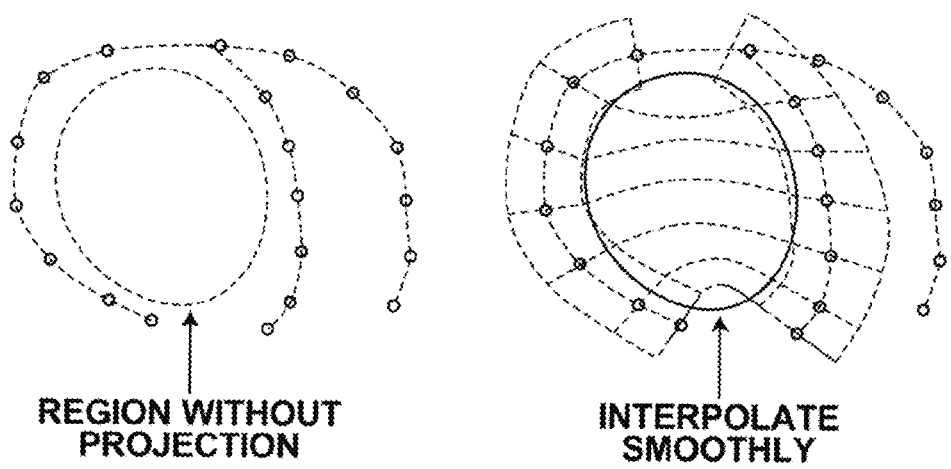
FIG. 13 is a diagram illustrating a manner of transforming an image that has been projected onto a ribbon-shaped projection surface to conform to reference points of a two-dimensional template (No. 2).

With respect to this region, a curved surface may be defined, as illustrated in FIG. 13, so that paths of the three-dimensional structure extraction data D corresponding to paths next to each other on the two-dimensional template 68 are smoothly connected to each other. Further, a ribbon-shaped projection surface S may be attached onto the curved surface, and three-dimensional volume data may be projected.

The length of a blood vessel of a subject has an individual difference. Therefore, the length of each blood vessel does not coincide with the length of each path of the two-dimensional template 68 in many cases. However, in observation of a plaque in a blood vessel, it is important that a relationship between the length of the blood vessel and the diameter of the blood vessel does not change. Therefore, the length of a path between reference points of the two-dimensional template 68 is changed, and projection is performed.

Specifically, when the length of a path between analysis points next to each other in the three-dimensional structure extraction data D and the length of a path between reference points in the two-dimensional template 68 that correspond to the analysis points are 1 to 1, the second projection means 652 should directly project the CPR image generated by the first projection means 651 based on the shape of the two-dimensional template 68. However, for example, when the length of a path between analysis points next to each other in the three-dimensional structure extraction data D and the length of a path between reference points in the two-dimensional template 68 that correspond to the analysis points are 2 to 1, the second projection means 652 should project the CPR image based on the shape of the two-dimensional template 68 after the positions of the reference points are adjusted so that the length of the corresponding path of the two-dimensional template 68 becomes twice the length. Such adjustment is performed for each of all segments so that the lengths of all the paths of the three-dimensional structure extraction data D are maintained on the two-dimensional template 68. When projection is performed in such a manner, the width of a path (the diameter of a blood vessel) is also maintained naturally. In this case, the length and the diameter of the blood vessel are kept, but the length of a path of the two-dimensional template 68 changes. Therefore, the shape of the two-dimensional template 68 changes slightly. However, it is desirable that the shape of a structure represented by the template is not substantially deformed when the length of the path in the two-dimensional template 68 is adjusted.

Alternatively, projection may be performed by changing the length of a blood vessel between reference points in a CPR image without changing the length of a path between reference points of the two-dimensional template 68. Specifically, the CPR image is enlarged or reduced in a direction in which the blood vessel runs. However, since it is necessary to observe a change at least in the diameter of a blood vessel to appropriately observe the blood vessel, projection is performed in such a manner that information about the diameter of the blood vessel is maintained.

For example, when the length of a path between analysis points next to each other in the three-dimensional structure extraction data D and the length of a path between reference points in the two-dimensional template 68 that correspond to the analysis points are 2 to 1, a CPR image of the path is reduced to ½ in the direction of the path. However, the CPR image is projected based on the shape of the two-dimensional template 68 at an actual size magnification ratio with respect to the direction of the width. This processing is performed for each of all segments, and projection is performed in such a manner that the widths of all paths in the three-dimensional structure extraction data D are maintained without changing the positions of all of the reference points in the two-dimensional template 68. In this case, the shape of the two-dimensional template 68 does not change.

Figure 14A:
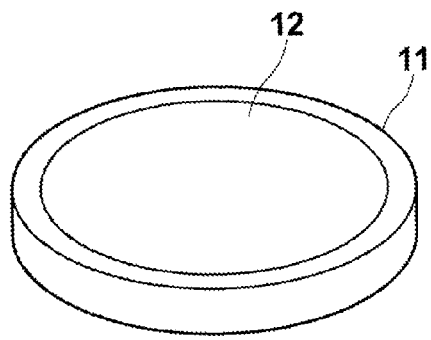
FIG. 14A is a diagram illustrating a cross section of a coronary artery region (without plaque).
Figure 14B:
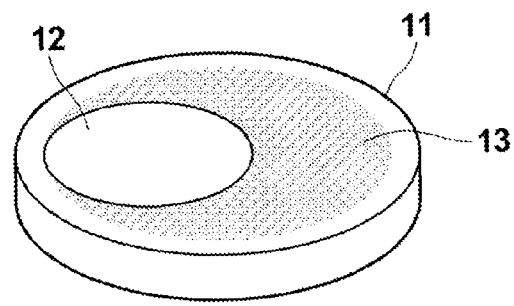
FIG. 14B is a diagram illustrating a cross section of a coronary artery region (with plaque).

Next, processing of the stenosis region detection means 66 will be described. The stenosis region detection means 66 detects a plaque at each analysis point in each of plural coronary artery regions extracted by the structure extraction means 62. FIGS. 14A and 14B are diagrams illustrating cross sections of coronary arteries at analysis points. FIG. 14A is a diagram illustrating a normal coronary artery, and FIG. 14B is a diagram illustrating a coronary artery in which a plaque has been deposited on the inner lining of the coronary artery.

The stenosis region detection means 66 identifies a lumen region 12 and a plaque region 13 in the coronary artery region 11. Generally, the CT value of a soft plaque is lower than the CT value of a normal lumen, but the CT value of a hard plaque is higher than the CT value of a normal lumen. It is well known that the signal value of a plaque is outside the range of signal values of a normal lumen not only in CT but also in MRI. Therefore, the stenosis region detection means 66 uses this relationship of signal values, and distinguishes the plaque region and the lumen region from each other. Specifically, the stenosis region detection means 66 judges whether each voxel represents a plaque or a lumen by comparing the value of each voxel constituting a cross section with a predetermined threshold value. The stenosis region detection means 66 identifies a region composed of voxels that have been judged to be a plaque, as the plaque region 13. The stenosis region detection means 66 identifies a region composed of voxels that have been judged to be a lumen, as the lumen region 12. With respect to the plaque, the stenosis region detection means 66 also distinguishes a soft plaque and a hard plaque from each other.

Figure 15:
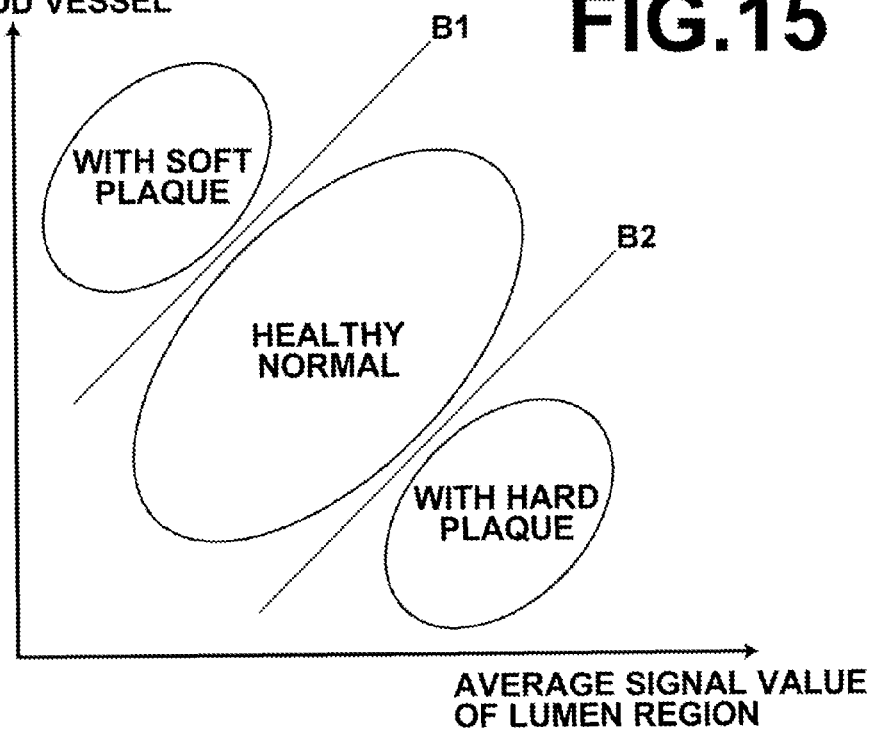
FIG. 15 is a diagram for explaining a method for identifying a region.

Here, since the range of possible signal values representing a lumen depends on the size of a blood vessel and a contrast condition, the range is not always uniform. Therefore, it is desirable to set a value that varies based on the size of a blood vessel, as the threshold value used for distinguishing a plaque region and a lumen region from each other. In the present embodiment, the threshold value is set as two boundary lines B1, B2, as illustrated in FIG. 15. The two boundary lines B1, B2 divide a coordinate plane that is defined by a horizontal axis representing signal values and a vertical axis representing diameters of blood vessels (an average of radii or diameters measured with respect to plural directions) into three sections. The boundary lines are set by preparing sample data about blood vessels having different sizes from each other with respect to normal blood vessels and blood vessels with plaque deposit, and by performing learning in advance. The set boundary lines are stored in the memory, and are referred to by the stenosis region detection means 66.

The stenosis region detection means 66 distinguishes whether a voxel represents a plaque (a soft plaque or a hard plaque) or a lumen based on which side of the boundary lines B1, B2 a coordinate point represented by (the signal value of the voxel and the diameter of a blood vessel) is located on the coordinate plane illustrated in FIG. 15. The stenosis region detection means 66 detects a region in which a plaque is present, as a stenosis region. Further, the size of a blood vessel has a correlation not only with the diameter of the blood vessel, but also with the area of the blood vessel.

Therefore, the vertical axis of the coordinate plane, in which the boundary lines are set in FIG. 15, may represent the area of the blood vessel.

Finally, processing of the display means 67 will be described. The display means 67 displays and outputs, on a display 7, a two-dimensional projection image that has been generated by the projection image generation means 65, and which has been projected along a path on the two-dimensional template. FIG. 16 is a diagram illustrating an example of displaying and outputting a two-dimensional projection image. When the stenosis region detection means 66 has detected a stenosis region, the display means 67 superimposes, on a two-dimensional projection image, an image in which a stenosis region is displayed in an emphasized manner using a different color to make a plaque recognizable, and displays and outputs the image on the display 7.

As described above in detail, when diagnosis is performed by using an image obtained by projecting a CPR image onto a two-dimensional template the shape of which is similar to a schema diagram, it is possible to efficiently find an abnormal region, such as a stenosis region, and an improvement in the efficiency of image reading is expected. Further, when a CPR image projected onto a two-dimensional template is used in an image reading report, the image is substituted for a schema diagram, and that is effective. In the above descriptions, a blood vessel was used as an example. However, the present invention may be applied to a tubular structure, such as bronchi.

In the above descriptions, a case in which a tubular structure is a tree-structure structure, such as coronary arteries, was used as an example. A CPR image projected onto a two-dimensional template may be generated in a similar manner even when a tubular structure includes a closed path, such as blood vessels of the brain, as illustrated in FIG. 17. Further, the present invention may be applied also to various blood vessels, such as the aorta.

In the above descriptions, a case of generating a projection image by CPR processing was described. Voxel values in a predetermined thickness may be averaged to generate an image. Alternatively, an image may be generated by MIP or MinIP processing.

In the above descriptions, when each path of a tubular structure of a two-dimensional template and each path of a tubular structure of three-dimensional structure extraction data are related to each other, a case of relating an analysis point and a reference point to each other by using the analysis point and the reference point, as specific points on paths, was described as an example. Alternatively, each path with a specific length may be related to each other.

Alternatively, a user may relate each path of a tubular structure of two-dimensional template and each path of a tubular structure of three-dimensional structure extraction data to each other.

In the above descriptions, a case in which a projection image generation program of the present invention is implemented in a WS for diagnosis, and functions as a projection image generation apparatus has been described. Alternatively, the projection image generation program may be distributed and installed in plural computers, and the plural computers may function as a projection image generation apparatus.

The invention claimed is:
1. A projection image generation apparatus comprising:
   a two-dimensional template storage that stores a two-dimensional template that two-dimensionally represents a schematic diagram of each path of a tubular structure composed of a plurality of three-dimension- ally branching paths, and in which a corresponding relationship of anatomical positions between positions on the paths of the tubular structure and positions on paths of the two-dimensional template has been set in advance, the two dimensional template being that in which plural reference points are set in advance as branching positions on the path of the tubular structure and paths connecting the reference points are set in advance;

one or more processors that operate as
  a structure extraction unit that obtains three-dimensional structure extraction data by extracting the tubular structure from volume data obtained by imaging a predetermined subject, and
  a relating unit that relates, based on the corresponding relationship, the positions on the paths of the two-dimensional template and the positions on the paths of the three-dimensional structure extraction data to each other; and
a projection image generator that generates a two-dimensional projection image by projecting voxel values of the tubular structure, where the voxel values are present along the paths of the three-dimensional structure extraction data, onto corresponding positions along the paths of the two-dimensional template, the projection image generator including
  a first projector that projects the voxel values of the tubular structure of the three-dimensional structure extraction data onto a ribbon-shaped projection surface defined along the paths of the three-dimensional structure extraction data in three-dimensional space, and
  a second projector that performs projection after transforming an image that has been projected onto the ribbon-shaped projection surface by the first projector to a shape on a corresponding path of the two-dimensional template so that the positions on the paths of the three-dimensional structure extraction data and the reference points of the two-dimensional template coincide with each other.

2. The projection image generation apparatus, as defined in claim 1, wherein the projection image generator performs projection in such a manner that the length of a blood vessel of the tubular structure present on the paths of the three-dimensional structure extraction data is maintained.

3. The projection image generation apparatus, as defined in claim 2, wherein the two-dimensional template is a schema diagram representing an anatomical characteristic of the tubular structure.

4. The projection image generation apparatus, as defined in claim 3, wherein the tubular structure is blood vessels.

5. The projection image generation apparatus, as defined in claim 2, wherein the tubular structure is blood vessels.

6. The projection image generation apparatus, as defined in claim 1, wherein the schematic diagram of the tubular structure represented by the two-dimensional template includes a closed path.

7. The projection image generation apparatus, as defined in claim 6, wherein the two-dimensional template is a schema diagram representing an anatomical characteristic of the tubular structure.

8. The projection image generation apparatus, as defined in claim 7, wherein the tubular structure is blood vessels.

9. The projection image generation apparatus, as defined in claim 6, wherein the tubular structure is blood vessels.

10. The projection image generation apparatus, as defined in claim 1, wherein the two-dimensional template is a schema diagram representing an anatomical characteristic of the tubular structure.

11. The projection image generation apparatus, as defined in claim 10, wherein the tubular structure is blood vessels.

12. The projection image generation apparatus, as defined in claim 1, wherein the tubular structure is blood vessels.

13. The projection image generation apparatus, as defined in claim 1, wherein the projection image generator performs projection in such a manner that a ratio of the diameter of the tubular structure at each position on the paths of the two-dimensional template corresponding to each position of the three-dimensional structure extraction data to the diameter of the tubular structure at each position on the paths of the three-dimensional structure extraction data is constant.

14. The projection image generation apparatus, as defined in claim 1, wherein the relating unit analyzes the branching position that exists on the path of the tubular structure in the three-dimensional structure extraction data and correlates the branching position in the three-dimensional structure extraction data to the reference point of the two dimensional template that are estimated to be the same points, and the position on the paths connecting the reference points corresponds to the position on the paths connecting the branching positions, which correspond to the reference points, of the tubular structure of the three-dimensional structure extraction data.

15. A non-transitory computer-readable recording medium storing therein a projection image generation program that causes a computer to function as:
  a two-dimensional template readout device that reads out a two-dimensional template from a two-dimensional template storage means storing the two-dimensional template that two-dimensionally represents a schematic diagram of each path of a tubular structure composed of a plurality of three-dimensionally branching paths, and in which a corresponding relationship of anatomical positions between positions on the paths of the tubular structure and positions on paths of the two-dimensional template has been set in advance, the two dimensional template being that in which plural reference points are set in advance as branching positions on the path of the tubular structure and paths connecting the reference points are set in advance;
  a structure extraction unit that obtains three-dimensional structure extraction data by extracting the tubular structure from volume data obtained by imaging a predetermined subject;
  a relating unit that relates, based on the corresponding relationship, the positions on the paths of the two-dimensional template and the positions on the paths of the three-dimensional structure extraction data to each other; and
  a projection image generator that generates a two-dimensional projection image by projecting voxel values of the tubular structure, where the voxel values are present along the paths of the three-dimensional structure extraction data, onto corresponding positions along the paths of the two-dimensional template, the projection image generator including
    a first projector that projects the voxel values of the tubular structure of the three-dimensional structure extraction data onto a ribbon-shaped projection surface defined along the paths of the three-dimensional structure extraction data in three-dimensional space, and a second projector that performs projection after transforming an image that has been projected onto the ribbon-shaped projection surface by the first projector to a shape on a corresponding path of the two-dimensional template so that the positions on the paths of the three-dimensional structure extraction data and the reference points of the two-dimensional template coincide with each other.

16. A projection image generation method that executes by a computer:

two-dimensional template readout processing that reads out a two-dimensional template from a two-dimensional template storage means storing the two-dimensional template that two-dimensionally represents a schematic diagram of each path of a tubular structure composed of a plurality of three-dimensionally branching paths, and in which a corresponding relationship of anatomical positions between positions on the paths of the tubular structure and positions on paths of the two-dimensional template has been set in advance, the two dimensional template being that in which plural reference points are set in advance as branching positions on the path of the tubular structure and paths connecting the reference points are set in advance;

structure extraction processing that obtains three-dimensional structure extraction data by extracting the tubular structure from volume data obtained by imaging a predetermined subject;

relating processing that relates, based on the corresponding relationship, the positions on the paths of the two-dimensional template and the positions on the paths of the three-dimensional structure extraction data to each other; and projection image generation processing that generates a two-dimensional projection image by projecting voxel values of the tubular structure, where the voxel values are present along the paths of the three-dimensional structure extraction data, onto corresponding positions along the paths of the two-dimensional template, the projection image generation processing including projecting the voxel values of the tubular structure of the three-dimensional structure extraction data onto a ribbon-shaped projection surface defined along the paths of the three-dimensional structure extraction data in three-dimensional space, and performing projection after transforming an image that has been projected onto the ribbon-shaped projection surface to a shape on a corresponding path of the two-dimensional template so that the positions on the paths of the three-dimensional structure extraction data and the reference points of the two-dimensional template coincide with each other.

* * * * *